United States Patent
Schrott et al.

(10) Patent No.: US 9,662,292 B2
(45) Date of Patent: May 30, 2017

(54) RINSE-OFF VOLUMIZING HAIR COMPOSITIONS CONTAINING STYLING POLYMERS AND POLYCATIONIC POLYMERS

(71) Applicant: KAO USA INC., Cincinnati, OH (US)

(72) Inventors: Adam Schrott, Cincinnati, OH (US); Elisabeth Cox, Cincinnati, OH (US)

(73) Assignee: Kao USA Inc., Cincinnati, OH (US)

( * ) Notice: Subject to any disclaimer, the term of this patent is extended or adjusted under 35 U.S.C. 154(b) by 255 days.

(21) Appl. No.: 14/518,271

(22) Filed: Oct. 20, 2014

(65) Prior Publication Data

US 2015/0110730 A1    Apr. 23, 2015

Related U.S. Application Data

(60) Provisional application No. 61/893,412, filed on Oct. 21, 2013.

(51) Int. Cl.
| | |
|---|---|
| *A61K 8/81* | (2006.01) |
| *A61Q 5/06* | (2006.01) |
| *A61K 8/88* | (2006.01) |

(52) U.S. Cl.
CPC .......... *A61K 8/8152* (2013.01); *A61K 8/8158* (2013.01); *A61K 8/8164* (2013.01); *A61K 8/8176* (2013.01); *A61K 8/8182* (2013.01); *A61K 8/88* (2013.01); *A61Q 5/06* (2013.01); *A61K 2800/30* (2013.01); *A61K 2800/33* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 6,025,501 | A * | 2/2000 | Ulmer | A61K 8/817 548/545 |
| 6,696,053 | B1 * | 2/2004 | Ma | A61K 8/8158 424/70.1 |
| 7,005,125 | B2 * | 2/2006 | Ulmer | A61K 8/8164 424/78.32 |
| 7,018,625 | B2 * | 3/2006 | Ulmer | A61K 8/8164 424/78.32 |
| 7,041,281 | B2 * | 5/2006 | Ulmer | A61K 8/8164 424/78.32 |
| 7,481,996 | B2 | 1/2009 | Ishii et al. | |
| 8,349,296 | B2 | 1/2013 | Cajan et al. | |
| 8,597,623 | B2 | 12/2013 | Hoffmann et al. | |
| 2006/0134049 | A1 * | 6/2006 | Keenan | A61K 8/81 424/70.15 |
| 2006/0159642 | A1 * | 7/2006 | Hanna | A61K 8/8141 424/70.7 |
| 2007/0110695 | A1 * | 5/2007 | Hoffmann | A61K 8/416 424/70.12 |
| 2008/0226575 | A1 * | 9/2008 | Hanna | A61K 8/817 424/70.7 |
| 2010/0247470 | A1 * | 9/2010 | Friel | A61K 8/06 424/70.7 |
| 2014/0196222 | A1 * | 7/2014 | Witte | A61K 8/37 8/406 |

FOREIGN PATENT DOCUMENTS

| | | | | |
|---|---|---|---|---|
| DE | EP 1712256 A1 * | 10/2006 | .......... | A61K 8/8158 |
| DE | EP 2269695 A1 * | 1/2011 | .......... | A61K 8/8158 |
| DE | 10 2011 083021 | 3/2013 | | |
| DE | 10 2011 089638 | 6/2013 | | |
| DE | 102011089638 * | 6/2013 | .............. | A61K 8/31 |
| EP | 1 779 838 | 5/2007 | | |
| WO | WO 01/82879 A2 | 11/2001 | | |
| WO | WO 2011133511 A1 * | 10/2011 | .............. | A61K 8/37 |
| WO | WO 2012075274 A1 * | 6/2012 | .......... | A61K 8/8164 |

OTHER PUBLICATIONS

Harry's Cosmeticology. Ed. M.M. Reiger. 8th ed. 2000, pp. 638-639.*
Buhler, V. Polyvinylpyrrolidone excipients for pharmaceuticals. Springer-Verlag (2005) ch. 2, pp. 5-6.*
Clements, Nancy. "Evaluating polyimide-1, a styling resin for gel and mousse formulations." Cosmetics and toiletries 120.3 (2005): 73-82.*
CAS Registry No. 869965-01-5 (Dec. 15, 2005).*
International Search Report and Written Opinion dated Jan. 30, 2015 for Application No. PCT/US2014/061495.
Gottshcalck, T.E., et al., eds., *International Cosmetic Ingredient Dictionary and Handbook*, Personal Care Products Council, Washington, D.C., 2012, vol. 1, p. xxiii, XP002734271.

* cited by examiner

*Primary Examiner* — Bethany Barham
*Assistant Examiner* — Peter Anthopolos
(74) *Attorney, Agent, or Firm* — Frost Brown Todd LLC

(57) ABSTRACT

Rinse-off of the volumizing compositions, having an acidic pH, and in the form of a lotion, gel or cream are disclosed. The compositions include one or more linear hairstyling polymers which exhibit polar behavior in acidic pH, such as polyvinylpyrrolidone, together with a selected group of polycationic hairstyling polymers, such as polyquaternium-37. The compositions not only provide a strong hair volumizing effect, but that effect is durable, being retained after two or more shampooing operations of the hair. The compositions are used by applying an effective amount to wet hair, leaving the composition for at least about three minutes, and rinsing the composition out of the hair.

9 Claims, No Drawings

RINSE-OFF VOLUMIZING HAIR COMPOSITIONS CONTAINING STYLING POLYMERS AND POLYCATIONIC POLYMERS

This application is based upon and claims priority from U.S. Provisional Patent Application Ser. No. 61/893,412, filed Oct. 21, 2013, which is incorporated herein by reference.

BACKGROUND

Providing fullness and volume to hair is a major benefit which can be provided by hair care compositions. This is particularly important for people having thin flat hair. This benefit makes the hair look healthy and allows the consumer to have a broader range of hair styles.

Generally, volumizing benefits are provided through the use of leave-on products (i.e., products which are applied to the hair and which are not rinsed off). Current hair volumizing products impart short-lived changes to the hair as a result of a relatively low level of styling polymer deposition. These products impart a film that washes out of the hair upon the next shampooing. These leave-on products, however, can result in the build-up of undesirable materials on the hair between washings.

The present invention is a rinse-off product which provides a hair volumizing benefit over an extended period of time even after the hair is shampooed several times. The present invention is a rinse-off product which is a new way to deliver hair volumizing benefits. The invention is unique in that it creates a film on the hair that not only provides an improved volume styling benefit, but is more substantive and longer lasting due to increased polymeric bonding at the hair surface in a low pH environment. This is accomplished using a combination of one or more linear hairstyling polymers of high polarity, together with a polycationic polymer in a low pH environment which, when included in a rinse-off hair treatment product, can result in the deposition of a substantive polymer film on the hair when delivered via a cationic lotion, gel or cream product. During styling, the polymer film allows networks of crosspoints to form between hair fibers; these crosspoints support, lift and separate the hair providing more body and volume.

U.S. Published Patent Application 2007/0110695, Hoffmann and Foerster (Kao Professional Salon Services), published May 17, 2007, relates to aqueous conditioning compositions for hair which are said to provide long-lasting conditioning effects even after several hair washes. The defined conditioning compositions comprise at least one polydimethylsiloxane having a viscosity of no greater than 350 mm²/S at a concentration of 12.5% by weight, together with from 0.2-5% by weight of polyquaternium 37.

SUMMARY

The present invention relates to rinse-off volumizing compositions, in the form of a lotion, gel or cream, having an acidic pH, comprising:

from about 0.5% to about 5% of one or more linear hair styling polymers which exhibit polar behavior in acidic pH; and
from about 0.01% to about 5% of one or more polycationic hairstyling polymers selected from homopolymers of trimethylaminoethyl methacrylate chloride (e.g., polyquaternium-37); copolymers of trimethylaminoethyl methacrylate chloride (e.g., polyquaternium-32); homopolymers of dimethyl ethyl aminoethyl methacrylate methosulfate; copolymers of dimethylethyl aminoethyl methacrylate methosulfate (e.g., polyquaternium-52), and mixtures thereof.

Examples of useful styling polymers include polyvinylpyrrolidone (PVP), vinylpyrrolidone vinylacetate (VP/VA) copolymers, polyimide-1, VP DMAPA acrylate copolymers, and mixtures of those materials. A preferred styling polymer is polyvinylpyrrolidone. A preferred polycationic polymer is polyquaternium-37.

The present invention also provides a method for providing long lasting volumizing properties to hair by applying an effective amount of a composition as defined herein to wet hair, leaving the composition on the hair for at least about three minutes, and rinsing the composition out of the hair.

As used herein, all percentages and ratios are "by weight" unless otherwise specified. Further, all patents, publications and other documents described in this patent application are incorporated herein by reference.

DETAILED DESCRIPTION

The present invention relates to rinse-off hair volumizing compositions which include at least one linear hairstyling polymer, together with a polycationic polymer which exhibits polar behavior in acidic pH, in a low pH environment which, when included in a rinse-off hair treatment product, can result in the deposition of a substantive polymer film on hair when delivered by a cationic lotion, gel or cream composition. During styling, the polymer film allows networks of crosspoints to form between hair fibers; these crosspoints support, lift and separate hair providing more body and volume.

In use, an effective amount of the treatment composition is applied to wet hair (for example, in the shower) after shampooing and, if desired, conditioning. It is left on the hair for a minimum of 3-5 minutes, and then rinsed out. After such treatment, the hair becomes much easier to style and it is easier to achieve voluminous styles. These benefits are durable and can last through multiple shampoo cycles.

The product will generally be in the form of a lotion, gel or cream. All of these product forms are well-known in the hair care art. A lotion would generally be more fluid than a conditioner and it spreads easily on the hair creating a high density cationic charge. A gel would generally be more translucent and viscous than a lotion, but would deliver the same technology and high density cationic charge to the hair. The polycationic polymer used herein is the source of the cationic charge in the composition and it imparts a high density cationic charge to the hair. It is this charge-based deposition onto the hair which allows the film to remain effective even after the hair is shampooed.

While the styling polymers defined herein are known to interact with hair fibers through hydrogen bonding and ionic interactions, the nature of the cationic lotion, gel or cream is such that the cationic polymer adsorbs onto the hair through ionic interactions to provide a volumizing benefit while also reducing the potential to rinse off the deposited styling polymers.

The full range of styling polymers useful in the present compositions will be defined hereinafter. However, the most preferred styling polymers for use herein are linear polymers having the potential to interact with one another and the hair fiber through ionic and hydrogen bonding. Examples of such polymers include polyvinylpyrrolidone (PVP), vinylpyrrolidone vinylacetate (VP/VA) copolymers, polyimide-1, and VP DMAPA acrylates copolymers. Polyvinylpyrrolidone is preferred. Usage level of the hairstyling polymers in the compositions of the present invention as low as about 0.5% and up to about 5.0%, have the volumizing effect on hair.

The compositions of the present invention also include polycationic hair care polymers. Polycationic polymers include those having an amino group or an ammonium group in the side chain of the polymer. They also can include a diallyl ammonium salt constituent. Examples of such polycationic polymers include homopolymers of trimethylaminoethyl methacrylate chloride (e.g., polyquaternium-37); copolymers of trimethylaminoethyl methacrylate chloride (e.g., polyquaternium-32); homopolymers of dimethyl ethyl aminoethyl methacrylate methosulfate; and copolymers of dimethylethyl aminoethyl methacrylate; and copolymers of dimethylethyl aminoethyl methacrylate methosulfate (e.g., polyquaternium-52); and mixtures of those materials. Polyquaternium-37 is preferred. The usage concentration of the polycationic polymer in the compositions of the present invention is from about 0.01% to about 5.0%, by weight, of the composition.

The compositions herein have a pH of from about 3.0 to about 6.0, in order to provide a good level of polymer film deposition on the hair. For example, some embodiments of the compositions herein can have a pH of from about 4.0 to about 5.5.

One of the benefits of the compositions herein is that they provide a durable polymer film on the hair which lasts and provides a volumizing benefit through shampoos, for example, through at least two, and up to about five shampoos/washes of the hair.

The volumizing compositions of the present invention are to be distinguished from other types of hair care compositions, such as shampoos, hair coloring products, and permanent wave compositions, which may incidentally include hairstyling polymers or even polycationic polymers. Those compositions do not include the combination of the hairstyling polymers together with the polycationic polymers in an acidic pH environment, in a rinse-off composition. Those compositions do not provide the durable volumizing benefit provided by the present invention. Thus, preferred compositions of the present invention are substantially free from anionic and nonionic surfactants, hair coloring materials, and hair waving materials. As used herein, "substantially free" means that the defined compositions contain less than about 2% (by weight of the composition), preferably less than about 1%, and more preferably less than about 0.5% of the defined materials which are limited for use in the compositions of the present invention. Preferred compositions are substantially free of all of these materials (i.e., the combined total of all the listed materials is less than about 2%, preferably less than about 1%, and more preferable less than about 0.5% of the composition). It is particularly important to minimize the amount of anionic materials in the compositions since they can neutralize the cationic charge and prevent binding of the cationic materials with the hair. Thus, one embodiment of the present invention is substantially free of anionic materials.

Linear hairstyling polymers which exhibit polar behavior at acidic pH are well-known in the hair care product formulation art. As used herein, the term "linear" is intended to define polymer chains without crosslinking or branching side chains; and the term "high polarity" is intended to mean that the polymer has the ability to assume a polar character when added to the acidic pH composition herein. Such polymers are, for example, disclosed in U.S. Pat. No. 7,481,996, Ishii et al, issued Jan. 27, 2009; and U.S. Pat. No. 8,349,296, Cajan et al, issued Jan. 8, 2013; both of which are incorporated herein by reference. They include, for example, nonionic polymers, cationic polymers and anionic polymers.

Examples of such hairstyling polymers useful herein include alkylacrylamide/acrylate/alkylaminoalkylacrylamide/polyethylene glycol methacrylate copolymers, as described in Japanese Published Patent Application 02-180911, incorporated herein by reference; alkylacrylamide/alkylaminoalkylacrylamide/polyethylene glycol methacrylate copolymers, as described in Japanese Published Patent Application 08-291206, incorporated herein by reference; acrylates/lauryl acrylate/stearyl acrylate/ethylamine oxide methacrylate copolymers, such as Diaformer Z-712, a product of Mitsubishi Chemical; vinylamine/vinyl alcohol copolymers, such as Diafix C601, a product of Mitsubishi Chemical; acrylic resin alkanolamine solution, such as Plascize L-9540B, a product of Goo Chemical; polyurethane-1, such as Luviset PUR, a product of BASF; polyquaternium-11, such as Gafquat 440, a product of ISP (Ashland); polyquaternium-28, such as Gafquat HS-100, a product of ISP (Ashland); vinylmethylether/ethylmaleate copolymers, such as Gantrez ES-225, a product of ISP (Ashland); PVP/vinylcaprolactam/DMAPA acrylate copolymers, such as Aquaflex SF40, a product of ISP (Ashland); isobutylene/ethylmaleimide/hydroxyethylmaleimide copolymers, such as Aquaflex FX-64, a product of ISP (Ashland); polyquaternium-55, such as Styleze W-20, a product of ISP (Ashland); vinylpyrrolidone/DMAPA acrylate copolymers, such as Styleze CC-10, a product of ISP (Ashland); vinylpyrrolidone/VA copolymers, such as PVPNA735, a product of ISP; polyvinylpyrrolidone (PVP), such as PVP K-30, K-60, K-90, available from Ashland; polyimide-1, such as Aquaflex XL-30, available from Ashland; polyquaternium-69, such as Aquastyle 300AF, available from Ashland; acrylate copolymers, such as Luviflex Soft, available from Akzo Nobel; and acrylates/diacetoneacrylamide copolymer, such as AMP-acrylates diacetoneacrylamide copolymer, available from Goo Chemical. Hairstyling polymers that require neutralization with a basic pH material to render them functional for styling are excluded for use in the compositions herein.

The compositions of the present invention may also include materials conventionally included in hair care products to achieve their standard usage, formulational and manufacturing benefits, used at their standard levels. For example, the compositions of the present invention can additionally include fragrances, preservatives, rheology control agents, agents to improve the aesthetic properties or application properties of the compositions, components to improve the processability of the compositions, hair conditioning materials, and anti-static materials, all used at their conventional levels.

In the process of the present invention, the hair is moistened (for example, by shampooing the hair), and an effective amount (for example, from about 6 mg to about 8 mg) of the composition of the present invention is applied to the hair and is worked through the hair. The composition is allowed to remain on the hair for at least about 3 minutes (for example, for from about 3 to about 5 minutes) and the composition is then rinsed out of the hair with water. The hair can then be dried. This treatment will provide a volumization lift to the hair which can last through multiple shampoos of the hair.

EXAMPLES 1-8

Compositions of the present invention, having the formulations set forth in the table below, are prepared as set forth below.

| wt/wt % | 1 | 2 | 3 | 4 | 5 | 6 | 7 | 8 |
|---|---|---|---|---|---|---|---|---|
| Water | Balance | Balance | Balance | Balance | Balance | Balance | Balance | Balance |
| Mallic Acid | 0.02 | 0.04 | | | | | 0.02 | |
| Citric Acid | | | 0.04 | 0.02 | | 0.02 | | |
| Lactic Acid | | | | | 0.01 | | | 0.01 |
| Hydroxypropyl Methylcellulose | 0.25 | | 0.50 | 0.25 | 0.25 | 0.25 | | |
| Hydroxylethyl Cellulose | 1.00 | | 1.00 | | 1.00 | | 1.00 | |
| Polyquaternium-32 (and) Paraffinum Liquidum (and) PPG-1 Trideceth-6 | | | 2.00 | | 0.50 | 1.50 | | |
| Polyquaternium-52 (and) Laureth-16 | 2.00 | | | 1.00 | | | | |
| Polyquaternium-37 | 0.01 | 1.00 | 0.10 | 0.01 | 0.50 | 0.50 | 2.00 | 1.00 |
| Isodecyl Neopentanoate | | | | 0.01 | | | 2.00 | |
| PPG-9 | 0.01 | | | | | | | |
| PPG-15 Strearyl Ether | | | | | | 1.00 | 1.00 | 2.00 |
| Dicaprylyl Carbonate | | 2.00 | | | | | | |
| Cetyl Alcohol | 1.00 | 0.50 | | | 0.50 | | | 0.60 |
| Cetearyl Alcohol | | | 0.50 | | | 0.60 | | |
| Steartrimonium Chloride | 0.02 | | | 0.01 | 0.10 | | 0.10 | |
| Stearalkonium Chloride | | 0.01 | 0.02 | | | 0.01 | | 0.05 |
| PVP | 2.00 | | 1.50 | | 1.50 | 0.50 | 0.50 | |
| VP/VA Copolymer | | 1.00 | 2.50 | | 1.00 | 0.50 | 2.00 | 2.00 |
| Polyquaternium-11 | | | | 5.00 | | | | |
| Vinyl Pyrrolldone, Dimethylamino-propyl Metacrylamide (VP/DMAPMA) | | | | | | 2.00 | | 0.50 |
| Polyquaternium-69 | 0.50 | | | | | | 1.00 | |
| Polyimide-1 | 0.50 | 1.50 | | 1.00 | 0.50 | | | 1.00 |
| Preservative | QS | QS | QS | QS | QS | QS | QS | QS |
| Fragrance | QS | QS | QS | QS | QS | QS | QS | QS |

These products are made as follows:

(1) add ingredients in order listed to main tank, with heat (to 60° C.);

(2) mix after each ingredient is added to ensure homogeneity prior adding the next ingredient;

(3) waxes and fatty alcohol are pre-melted in a separate container (heated to 70-75° C.), and are added to the main tank when melted; and (4) cool the mixture to 40° C. prior to incorporating the preservative and fragrance ingredients.

These compositions, when used as described in this application, provide hair with a durable volumizing benefit.

EXAMPLE 9

A tress test was conducted in which the volumizing effects of a traditional volumizing mousse was compared to the volumizing effects of the volume treatment composition of the present invention. The composition of the present invention is a rinse-off application. The traditional volumizing mousse is a leave-on application. In this test, the traditional volumizing mousse was a commercialized hair care product, the components of which are summarized in the following table:

| Ingredient | W/W % |
|---|---|
| Deionized water | QS to 100 |
| VP/Methacrylamide/Vinyl Imidazole Copolymer | 9-12% |
| Polyquaternium-46 | 4-7% |
| Propylene Glycol + Diazolidinyl Urea + Methylparaben + propylparaben | <1% |
| Ceteareth-25 | <1% |
| Cocotrimonium methosulfate | <1% |
| Laureth-3 | <1% |
| Fragrance | <1% |
| Benzophenone-4 | <1% |
| Panthenol | <1% |
| Finished Product | |
| Mousse bulk | 94.25% |
| Propellant | 5.75% |

The composition of the present invention which was tested had the following formulation:

| W/W % | |
|---|---|
| Water | Balance |
| Malic Acid | 0.02-0.5% |
| Hydroxypropyl Methylcellulose | 0.1-1.0% |
| Polyquaternium-37 | 0.1-5% |
| Isodecyl Neopentanoate | 0.5-5% |
| Cetyl Alcohol | 0.1-1.0% |
| Steartrimonium Chloride | 0.02-0.4% |
| PVP | 0.5-5% |
| VP/VA Copolymer | 0.5-5% |
| Polyimide-1 | 0.5-5% |

| W/W % | |
|---|---|
| Preservative | QS |
| Fragrance | QS |

Procedure for making:
1. Add ingredients in order listed to main tank with heat (to 60 C),
2. Mixing after each ingredient to ensure homogeneity prior to adding next ingredient.
3. Note: Pre-melt waxes/fatty alcohol, etc. in separate container (heat to 70-75 C). Add to main tank when melted.
4. Cool to 40 C prior to incorporating preservative and fragrance ingredients.

The tresses used were 3"×3" rubber sheet tresses, medium blonde hair type with 250 fibers per tress. The test method used for this test included the following steps:

(1) Shampoo each tress with 1.5 ml of 10% sodium laureth sulfate solution.

(2) Lather each tress for 30 seconds.

(3) Rinse each tress with water for 30 seconds.

(4) Squeeze out excess water from each tress.

(5) Apply 2.5 grams of the volumizing product to each tress. For the present invention, leave the composition on the hair for 5 minutes before rinsing. For the traditional volumizing mousse, leave the product on the tress; do not rinse.

(6) Blow-dry the tresses, combing with a vent brush until dry.

(7) Flip the tresses over against the growth pattern. Measure root lift with a Vernier caliper in the center of each tress (1.5"×1.5").

(8) Repeat steps (1), (3) and (4) five times, taking measurements of root lift in the center of the tress after three and five shampoos.

The results from the test are summarized in the following table:

| | Δ Root Lift Present Invention | Δ Root Lift Conventional Mousse |
|---|---|---|
| After 3 Shampoos | −1.79 mm (−4.9%) | −10.53 mm (−41.2%) |
| After 5 Shampoos | −7.02 mm (−19.5%) | −10.68 mm (−41.8%) |

The data demonstrate that the loss in root lift (i.e., the loss in volume of the hair) was significantly less for the compositions and treatment of the present invention after both three and five shampoos, when compared to the volume loss demonstrated with the standard volumizing product after shampooing three and five times.

EXAMPLE 10

A tress test was conducted in which the volumizing effects of the compositions and method of the present invention were compared to the volumizing effects of the compositions disclosed in U.S. Published Patent Application 2007/0110695. The composition of the present invention which was tested is the same one as was utilized in Example 9. The composition from the prior art patent which was tested had the following formulation:

| | | Batch Size wt % of composition | 500.00 g. wt/batch |
|---|---|---|---|
| A | Deionized Water | 73.830 | 369.150 |
| | Behetrimonium Chloride | 2.000 | 10.000 |
| B | Polyquaternium-37 | 1.000 | 5.000 |
| | Dimethicone (DC 200 Fluid 5 cst) | 19.000 | 95.000 |
| | Phenyl Trimethicone (DC556) | 0.500 | 2.500 |
| C | Ethylhexyl Methoxycinnamate (Octinoxate USP) | 0.500 | 2.500 |
| | Kathon | 0.070 | 0.350 |
| | Benzyl Alcohol | 2.000 | 10.000 |
| | Fragrance | 0.600 | 3.000 |
| | QS/NaOH or Citric Acid, pH = 4.75 | 0.500 | 2.500 |
| | Totals | | 500 |

The tresses used in the test were 3"×3" rubber sheet tresses, medium blonde hair type having 250 fibers per tress. The test method for this test included the following steps:

(1) Each tress was shampooed with 1.5 ml of 10% sodium laureth sulfate solution.

(2) Each tress was lathered for 30 seconds.

(3) Each tress was rinsed with water for 30 seconds.

(4) Excess water was squeezed out of each tress.

(5) 2.5 grams of product was applied to each tress. For both treatments, the treatment was left on the hair for 5 minutes before rinsing.

(6) Each tress was blow-dried, combing with a vent brush until dry.

(7) Each tress was flipped over against growth pattern. The root lift was measured with a Vernier caliper in the center of the tress (1.5"×1.5").

(8) Repeat steps (1), (3) and (4) five times, taking measurements of root lift in the center of the tress after three and five shampoos.

The results from the comparative study is shown in the following table.

| | Δ Root Lift Present Invention | Δ Root Lift Prior Art Treatment |
|---|---|---|
| After 3 Shampoos | −1.38 mm (−3.8%) | −4.03 mm (−19.7%) |
| After 5 Shampoos | −3.48 mm (−9.5%) | −4.68 mm (−22.9%) |

As can be seen from the data, the composition and method of the present invention showed a much smaller loss of hair volume after both three and five shampoos, compared to the hair volume loss shown by the prior art treatment after both three and five shampoos.

What is claimed is:

1. A rinse-off hair volumizing composition, in the form of a lotion, gel or cream, having an acidic pH, comprising:
   from about 0.5% (by wt.) to about 5% (by wt.) of a mixture of polyvinylpyrrolidone (PVP) and polyimide-1; and
   from about 0.01% (by wt.) to about 5% (by wt.) of one or more polycationic hairstyling polymers selected from homopolymers of trimethylaminoethyl methacrylate chloride; copolymers of trimethylaminoethyl methacrylate chloride; homopolymers of dimethyl ethyl aminoethyl methacrylate methosulfate; copolymers of dimethylethyl aminoethyl methacrylate methosulfate; and mixtures thereof.

2. The composition according to claim 1 having a pH of from about 3 to about 6.

3. The composition according to claim 1 wherein the polycationic hairstyling polymer is selected from polyquaternium-37, polyquaternium-52, polyquaternium-32, and mixtures thereof.

4. The composition according to claim 3 wherein the polycationic hairstyling polymer is polyquaternium-37.

5. A rinse-off hair volumizing composition, in the form of a lotion, gel or cream, having an acidic pH, comprising:
   from about 0.5% (by wt.) to about 5% (by wt.) of a mixture of vinylpyrrolidone vinylacetate (VP/VA) and polyimide-1; and
   from about 0.01% (by wt.) to about 5% (by wt.) of one or more polycationic hairstyling polymers selected from homopolymers of trimethylaminoethyl methacrylate chloride; copolymers of trimethylaminoethyl methacrylate chloride; homopolymers of dimethyl ethyl aminoethyl methacrylate methosulfate; copolymers of dimethylethyl aminoethyl methacrylate methosulfate; and mixtures thereof.

6. The composition according to claim 5 having a pH of from about 3 to about 6.

7. The composition according to claim 5 wherein the polycationic hairstyling polymer is selected from polyquaternium-37, polyquaternium-52, polyquaternium-32, and mixtures thereof.

8. The composition according to claim 7 wherein the polycationic hairstyling polymer is polyquaternium-37.

9. A method for providing volumizing properties to hair by applying an effective amount of the composition of claim 5 to wet hair, leaving the composition on the hair for at least about three minutes, and rinsing the composition out of the hair.

* * * * *